US011071800B2

(12) United States Patent
Matta et al.

(10) Patent No.: US 11,071,800 B2
(45) Date of Patent: *Jul. 27, 2021

(54) SYSTEMS AND METHODS FOR USING SOLID HIGH-LEVEL DISINFECTION CHEMISTRIES TO PRODUCE DISINFECTANT SOLUTIONS

(71) Applicant: Medivators inc., Minneapolis, MN (US)

(72) Inventors: John Matta, Shoreview, MN (US); Huyen Bui, Brooklyn Park, MN (US); Tuan Nguyen, Chaska, MN (US)

(73) Assignee: Medivators Inc., Minneapolis, MN (US)

( * ) Notice: Subject to any disclaimer, the term of this patent is extended or adjusted under 35 U.S.C. 154(b) by 63 days.

This patent is subject to a terminal disclaimer.

(21) Appl. No.: 16/337,009

(22) PCT Filed: Sep. 28, 2017

(86) PCT No.: PCT/US2017/053932
§ 371 (c)(1),
(2) Date: Mar. 27, 2019

(87) PCT Pub. No.: WO2018/064290
PCT Pub. Date: Apr. 5, 2018

(65) Prior Publication Data
US 2019/0224355 A1    Jul. 25, 2019

Related U.S. Application Data

(60) Provisional application No. 62/400,774, filed on Sep. 28, 2016, provisional application No. 62/452,666, filed on Jan. 31, 2017.

(51) Int. Cl.
*B01J 19/18* (2006.01)
*A61L 2/18* (2006.01)
(Continued)

(52) U.S. Cl.
CPC .............. *A61L 2/186* (2013.01); *A01N 37/16* (2013.01); *A61L 2/23* (2013.01); *B01J 19/1862* (2013.01);
(Continued)

(58) Field of Classification Search
CPC .. A61L 2/186; A61L 2202/24; A61L 2202/11; B01J 19/1862; B01J 2219/00281; B01J 2219/0072; B01J 2219/0059
See application file for complete search history.

(56) References Cited

U.S. PATENT DOCUMENTS 5,116,575 A    5/1992  Badertscher et al.
5,350,563 A    9/1994  Kralovic et al.
(Continued)

FOREIGN PATENT DOCUMENTS

CA    2569025    6/2008
CN    1128257    8/1996
(Continued)

OTHER PUBLICATIONS

International Search Report and Written Opinion of the International Searching Authority dated Dec. 11, 2017, of International PCT Application No. PCT/US2017/053932 filed Sep. 28, 2017.
(Continued)

*Primary Examiner* — Lessanework Seifu (57) ABSTRACT

Systems and methods for using solid high-level disinfection chemistries to producing disinfectant solutions. In an embodiment, an apparatus comprises: a first container and a second container. The first container is configured to receive water, sodium percarbonate and tetraacetylethylenediamine. The water, the sodium percarbonate, the tetraacetylethylenediamine react within the first container to produce a mixture comprising peroxyacetic acid. The second container is in fluid communication with the first container, wherein the
(Continued)

second container is configured to receive an acid and the mixture. The mixture and the acid mix in the second container to produce a disinfectant solution having a pH between 5.0 and 7.0.

10 Claims, 4 Drawing Sheets

(51) Int. Cl.
| | | |
|---|---|---|
| *A61L 2/23* | (2006.01) | |
| *A01N 37/16* | (2006.01) | |
| *C11D 3/39* | (2006.01) | |
| *C11D 3/48* | (2006.01) | |
| *B01J 16/00* | (2006.01) | |

(52) U.S. Cl.
CPC ........ *A61L 2202/11* (2013.01); *A61L 2202/24* (2013.01); *B01J 16/00* (2013.01); *B01J 2219/0059* (2013.01); *B01J 2219/0072* (2013.01); *B01J 2219/00281* (2013.01); *C11D 3/3947* (2013.01); *C11D 3/48* (2013.01)

(56) References Cited

U.S. PATENT DOCUMENTS

| | | | |
|---|---|---|---|
| 7,235,252 B2 | 6/2007 | Preto et al. | |
| 8,920,715 B2 | 12/2014 | Roberts et al. | |
| 9,517,955 B2 | 12/2016 | Buschmann | |
| 9,701,931 B2 | 7/2017 | Moore | |
| 2002/0182103 A1* | 12/2002 | Biering | A01N 37/16 422/28 |
| 2005/0153854 A1 | 7/2005 | Meyer et al. | |
| 2007/0184999 A1 | 8/2007 | Dicosimo et al. | |
| 2009/0142235 A1 | 6/2009 | Rico et al. | |
| 2011/0293472 A1 | 12/2011 | McSherry et al. | |
| 2012/0108878 A1 | 5/2012 | Conrad | |
| 2014/0039051 A1 | 2/2014 | Strodtholz et al. | |
| 2016/0270389 A1 | 9/2016 | Glasbey | |
| 2016/0286800 A1 | 10/2016 | Dagher et al. | |

FOREIGN PATENT DOCUMENTS

| | | |
|---|---|---|
| CN | 101564546 | 10/2009 |
| CN | 102964285 | 3/2013 |
| CN | 103204793 | 7/2013 |
| CN | 104479888 | 4/2015 |
| GB | 2522074 | 7/2015 |
| JP | 2001072518 | 3/2001 |
| JP | 2001505896 | 5/2001 |
| JP | 2010506901 | 3/2010 |
| JP | 2015002855 | 1/2015 |
| WO | 2016055773 A1 | 4/2016 |
| WO | 2016082897 A1 | 6/2016 |

OTHER PUBLICATIONS

International Search Report and Written Opinion of the International Searching Authority dated Dec. 12, 2017, of International PCT Application No. PCT/US2017/053934 filed Sep. 28, 2017.
International Preliminary Report on Patentability issued in PCT/US2017/053932, dated Apr. 11, 2019.
International Preliminary Report on Patentability issued in PCT/US2017/053934, dated Apr. 11, 2019.
Xiandai Yiyuan Xiaoduxue/Chief Editors: Yang Huaming and Yi Bin,—3rd Edition,—Beijing: People's Military Medical Press, Feb. 2013 ISBN 978-7-5091-6402-0.

* cited by examiner

FIG. 4

SYSTEMS AND METHODS FOR USING SOLID HIGH-LEVEL DISINFECTION CHEMISTRIES TO PRODUCE DISINFECTANT SOLUTIONS

CROSS REFERENCE TO RELATED APPLICATIONS

This application claims priority to U.S. Provisional Patent Application Ser. No. 62/400,774 filed Sep. 28, 2016 and also claims priority to U.S. Provisional Patent Application Ser. No. 62/452,666 filed Jan. 31, 2017. These applications are incorporated herein by reference, in their entireties.

TECHNICAL FIELD

Embodiments of the present disclosure relate to disinfectant solutions. More specifically, embodiments of the present disclosure relate to producing disinfectant solutions from solid chemistries, which are used for disinfecting a medical device.

BACKGROUND

Many medical devices may be reused on different patients. Before a medical device is used on a subsequent patient, however, the medical device may need to be reprocessed. For example, after an endoscope is used on a patient, a number of steps are required to reprocess the endoscope, so that the endoscope can be used on another patient. Included in the steps of reprocessing an endoscope is disinfecting an endoscope, using a disinfectant solution. Conventionally, liquid disinfectants are shipped by a manufacturer to a hospital or other facility. The hospital or other facility then uses the liquid disinfectant chemistries to disinfect an endoscope.

SUMMARY

Embodiments of the present disclosure relate to apparatus and methods for producing disinfectant solutions from solid chemistries, for use with disinfecting a medical device. Example embodiments include, but are not limited to, the following.

In one aspect, the invention is directed to an apparatus configured to produce a disinfectant solution for use with disinfecting a medical device. The apparatus includes a first container configured to receive water, sodium percarbonate and tetraacetylethylenediamine, wherein the water, the sodium percarbonate and the tetraacetylethylenediamine react within the first container to produce a mixture comprising peroxyacetic acid and having a pH between 9.0 and 14.0; and a second container in fluid communication with the first container, the second container configured to receive an acid and the mixture from the first container, wherein the mixture and the acid mix in the second container to produce a disinfectant solution having a pH between 5.0 and 7.0.

In another aspect, the invention is directed to a method for producing a disinfectant solution for disinfecting a medical device. The method includes combining water, sodium percarbonate and tetraacetylethylenediamine to produce a mixture comprising peroxyacetic acid, wherein the peroxyacetic acid has a concentration of at least 500 parts per million; combining an acid with the mixture to form the disinfectant solution having a pH between 5.0 and 7.0; and contacting a medical device with the disinfectant solution within 24 hours of forming the disinfectant solution. In one embodiment, the disinfectant solution may contact a medical device between 5 minutes to 10 minutes. Alternatively, the disinfectant solution may contact the medical device for a shorter period of time or a longer period of time.

In another aspect, the invention is directed to an apparatus configured to produce a disinfectant solution for use with disinfecting a medical device. The apparatus includes a first container including sodium percarbonate and tetraacetylethylenediamine. The first container includes a first aperture configured to receive water, wherein the water, the sodium percarbonate and the tetraacetylethylenediamine react within the first container to produce a mixture comprising peroxyacetic acid. In one embodiment, the first container is configured to filter undissolved portions of the sodium percarbonate and the tetraacetylethylenediamine. The first container includes a second aperture that the mixture exits through. A second container is configured to receive the mixture from the first container via the second aperture, the second container comprising an acid, wherein the mixture and the acid mix in the second container to produce a disinfectant solution having a pH between 5.0 and 7.0.

In another aspect, the invention is directed to a method including providing, to a user, sodium percarbonate and tetraacetylethylenediamine in a first compartment of a package and an acid in a second compartment of the package; providing instructions to the user to combine the sodium percarbonate and the tetraacetylethylenediamine with water, wherein the water, sodium percarbonate, tetraacetylethylenediamine react within the first container to produce a mixture comprising peroxyacetic acid; and providing instructions to the user to combine the mixture with the acid, wherein the mixture and the acid produce a disinfectant solution for use with disinfecting a medical device, wherein the disinfectant solution has a pH between 5.0 and 7.0.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

DETAILED DESCRIPTION

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about." and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

As stated above, conventionally, liquid disinfectant chemistries are shipped by a manufacturer to a hospital or other facility that uses the liquid disinfectant chemistries to disinfect medical devices. Shipping liquid disinfectant chemistries, however, may have a number of drawbacks including, but not limited to, higher shipping costs than solid chemistries, limited shelf life, restricted method of shipment (e.g., only ground shipments) and/or the like. Accordingly, there is a need in the art for improved disinfectant chemistries used to disinfect medical devices.

While the present disclosure discusses using a solid high-level disinfectant for disinfecting an endoscope, in some embodiments, the solid high-level disinfectant may be used on other medical devices, as well. As such, the present disclosure is not limited to using the solid high-level disinfectant, as disclosed herein, when disinfecting an endoscope.

Figure 1:
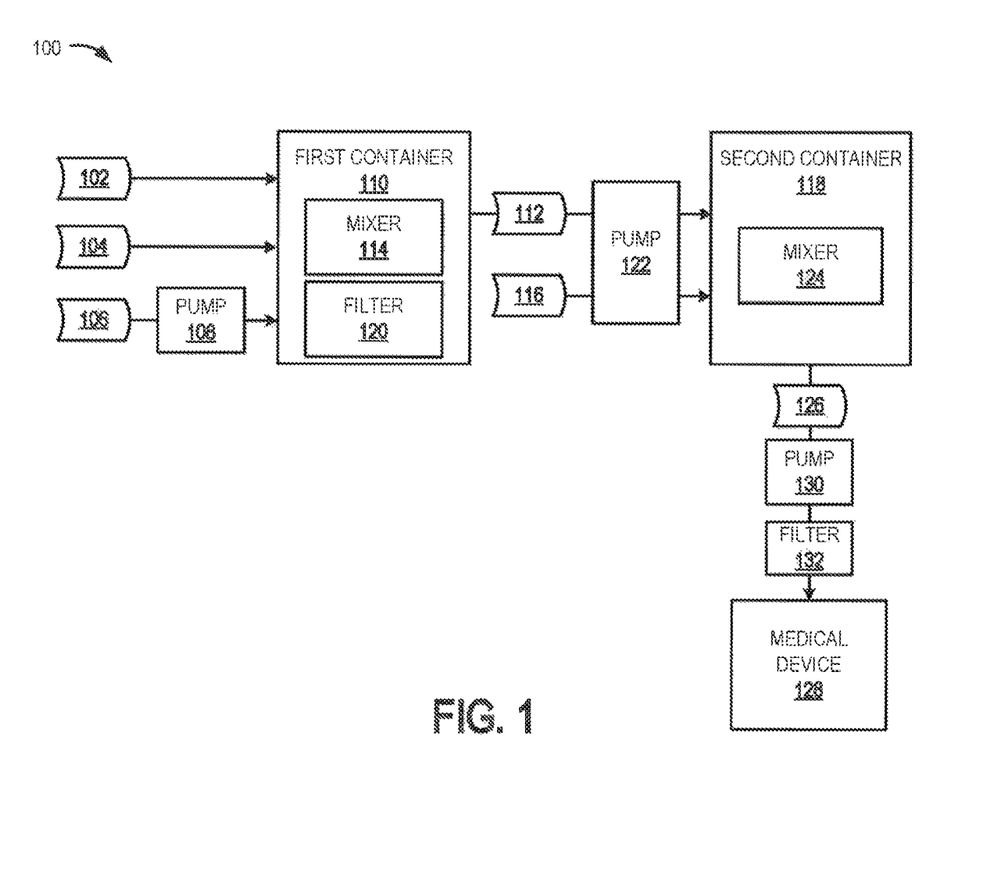
FIG. 1 is a schematic block diagram of an illustrative disinfectant system for use with disinfecting a medical device, in accordance with some embodiments of the present disclosure.

FIG. 1 is a schematic block diagram of an illustrative system 100 for producing a disinfectant for disinfecting a medical device, in accordance with some embodiments of the present disclosure. Due to the illustrative system 100, solid chemistries 102, 104 may be shipped to a hospital or other facility, instead of liquid disinfectant chemistries. As such, shipping costs may be reduced. Additionally or alternatively, in some embodiments, the solid chemistries 102, 104 may be shipped by air instead of ground and/or the solid chemistries 102, 104 may be more stable than liquid disinfectant chemistries. Additionally or alternatively, in some embodiments, the solid chemistries 102, 104 may be non-hazardous and the byproducts produced by the system 100, using the solid chemistries 102, 104, may be biodegradable, non-toxic and non-sensitizing. Additionally or alternatively, in some embodiments, the pH of a disinfectant produced by the system 100 may be approximately neutral, so that neutralization may not be required before disposal of the disinfectant. Additionally or alternatively, a disinfectant solution produced by the system 100 may be produced on site by the facility that uses the disinfectant solution to disinfect a medical device, so that the stability of the disinfectant solution may not be as imperative as other disinfectant solutions that are not produced on site.

As stated above, the system 100 includes solid chemistries 102, 104. Additionally, in some embodiments, the system 100 may include a liquid 106, a pump 108 and a first container 110. In embodiments, the solid chemistries 102, 104 and the liquid 106 may be coupled to the first container via one or more conduits (not shown). In some embodiments, the solid chemistries 102, 104 may be combined with the liquid 106 in the first container 110 to produce a fluid mixture 112. In some embodiments, the first container 110 may be made of any material capable of retaining the solid chemistries 102, 104 before and/or after the solid chemistries are combined with the liquid 106. For example, the first container 110 may be glass, plastic, metal, and/or the like.

In some embodiments, to facilitate the combination of the solid chemistries 102, 104 and the liquid 106, the pump 108 may pump the liquid 106 into the first container 110 at a first flow rate. The first flow rate may be a turbulent flow, which may facilitate the combination of the solid chemistries 102, 104 and the liquid 106 in the first container 110. Examples of first flow rates that may be produced by the pump 108 pumping the liquid 106 into the first container 110 include greater than about 0.5 gallons minute (gal/min), greater than about 0.75 gal/min, greater than about 1.0 gal/min, greater than about 1.25 gal/min), greater than about 1.5 gal/min, greater than about 1.75 gal/min, greater than about 2.0 gal/min and/or the like. However, these are only examples and not meant to be limiting.

Additionally or alternatively, to facilitate the combination of the solid chemistries 102, 104 and the liquid 106, a mixer 114 may be incorporated into, included in, and/or coupled to the first container 110. Before, during or after the liquid 106 is disposed in the first container 110, the mixer 114 may be started, so that when the liquid 106 is in the first container, the mixer 114 can facilitate combining the solid chemistries 102, 104 and the liquid 106. The mixer may be any kind of mixing device that is capable of mixing liquids.

The solid chemistries 102, 104 and the liquid 106 are selected to form a disinfectant mixture. In some embodiments, the solid chemistries 102, 104 may be sodium percarbonate and tetraacetylethylenediamine (TAED), respectively, and the liquid 106 may be water. Additionally or alternatively, one of the solid chemistries may be sodium perborate. In some embodiments where the solid chemistry 102 is sodium percarbonate and the liquid 106 is water, the sodium percarbonate may dissolve in water 106 to produce sodium carbonate and hydrogen peroxide, according to equation (1):

(1)

In some embodiments, the hydrogen peroxide resulting from the reaction of water and sodium percarbonate may have concentrations between approximately 3000 ppm and 6000 ppm, specifically between 4000 ppm and 5000 ppm. In some embodiments, the hydrogen peroxide produced by dissolving the sodium percarbonate in water reacts with the TAED to produce peroxyacetic acid (also known as peracetic acid), a main ingredient used to disinfect an endoscope, and diacetylethylenediamine (DAED), according to equation (2):

(2)

In some embodiments, the fluid mixture 112 that is produced by the combination of the solid chemistries 102, 104 and the liquid 106 may include peroxyacetic acid produced according equation (2). In some embodiments, the fluid mixture 112 may also include the DAED that is produced according equation (2).

In some embodiments, to facilitate the reaction of the hydrogen peroxide and TAED, the water in which the sodium percarbonate dissolves may be at a desired temperature. In some embodiments, the water may be greater than or equal to about 30° C., 35° C., 40° C., 50° C., 60° C., 70° C., 80° C., 90° C., 100° C. and/or the like since a temperature of 30° C. may facilitate the reaction of the hydrogen peroxide, produced from the sodium percarbonate in water, and the TAED.

In some embodiments, sodium percarbonate, TAED and water may be provided in amounts to create a desired amount of peroxyacetic acid. For example, sodium percarbonate, TAED and water may be provided in sufficient amounts to produce peroxyacetic acid in concentrations between: about 500 parts per million (ppm) and about 2200 ppm, between about 800 parts per million (ppm) and about 1600 ppm, between about 1000 ppm and about 1400 ppm, approximately 1200 ppm, and/or the like. As another example, the amount of desired peroxyacetic acid produced may be greater than: about 500 ppm, about 800 ppm, about 1000 ppm, about 1200 ppm, about 1400 ppm, about 1600 ppm and/or the like. As even another example, the amount of desired peroxyacetic acid produced may be between less than: about 1600 ppm, about 1400 ppm, about 1200 ppm, about 1000 ppm, about 800 ppm, about 500 ppm, and/or the like. However, these are only examples and not meant to be limiting. In one example, to produce peroxyacetic acid in quantities between about 1200 ppm and about 1500 ppm, about 4 liters of water may be combined with about 213 grams (g) of TAED and about 16.6 g of sodium percarbonate. This example is given for illustration purposes only and not meant to be limiting.

The fluid mixture 112 produced from the combination of the solid chemistries 102, 104 and the liquid 106 may have a pH of approximately between 9 and 14. A fluid mixture 112 with a high pH (i.e., above a pH of about 9) may corrode materials more quickly than a mixture with a lower pH (i.e., a pH of about 7 or lower). A fluid mixture 112 with a high pH may also have a strong odor. As such, if the fluid mixture 112, which has a high pH, were used to disinfect a medical device, the fluid mixture 112 may have to be neutralized after the fluid mixture 112 is used to disinfect a medical device, but before disposing of the fluid mixture 112. Accordingly, in embodiments, the pH of the fluid mixture 112 may be lowered.

To lower the pH of the fluid mixture 112, the fluid mixture 112 may be combined with an acid 116, wherein the acid 116 is originally in powder form. As illustrated in FIG. 1, the fluid mixture 112 may be transferred to a second container 118 and combined with the acid 116. Alternatively, the acid 116 may be added to the fluid mixture 112 in the first container 110. In some embodiments, the first container 110 and the second container 118 may be coupled to each other via one or more conduits (not shown). In some embodiments, the second container 118 may be any container capable of retaining the fluid mixture 112 and the acid 116. For example, the second container 118 may be made of glass, plastic, metal and/or the like.

In some embodiments, the solid chemistries 102, 104 and the acid 116 may be included in a single package and shipped to a facility that combines the solid chemistries 102, 104 with a liquid, as described above, and then combines the acid 116 with the mixture resulting from the mixture of the solid chemistries 102, 104 and the liquid. In some embodiments, the solid chemistries 102, 104 and the acid 116 are included in different compartments of the single package. As described above, this may eliminate the drawbacks of shipping a liquid disinfectant. For example, by shipping solid chemistries 102, 104 and an acid 116, shipping costs may be less than when shipping liquid disinfectants, the shelf life of the solid chemistries 102, 104 and the acid 116 may be longer than liquid disinfectants, and the solid chemistries 102, 104 and the acid 116 may be shipped via more methods than shipping liquid disinfectants (e.g., via air).

In some embodiments, before the fluid mixture 112 is neutralized with the acid 116, the fluid mixture 112 may be filtered using a filter 120. While the filter 120 is illustrated as being disposed in the first container 110, in some embodiments, the filter 120 may be coupled to an outlet of the first container 110, coupled to an inlet of the second container 110, coupled to and/or incorporated into a conduit that connects the first container 110 to the second container 118, incorporated into the first container 110, disposed between the first and second containers 110, 118 and/or the like. Additionally or alternatively, the first container 110 may be made of such a material that the first container 110 acts as the filter 120, as described below in relation to FIG. 2.

In some embodiments, the filter 120 may be a filter capable of filtering undissolved portions of the solid chemistries 102, 104. For example, in one embodiment, the fluid mixture 112 is directed through filter 120, and filter 120 prevents large particles or items from passing through the filter (i.e., undissolved portions of the solid chemistries 102 and/or 104), while allowing the fluid mixture 112 to pass through the filter 120. For example, the filter 120 may be a 100 micron filter (i.e., the average pore size is 100 microns), a 20 micron filter (i.e., the average pore size is 20 microns), a 10 micron filter (i.e., the average pore size is 10 microns), a 5 micron filter (i.e., the average pore size is 5 microns), a 1 micron filter (i.e., the average pore size is 1 micron), a 0.5 micron filter (i.e., the average pore size is 0.5 microns), a 0.1 micron filter (i.e., the average pore size is 0.1 microns) and/or the like.

In embodiments where the fluid mixture 112 is combined with the acid 116 in a second container 118, the fluid mixture 112 may be transferred to the second container 118 by the pump 108. Additionally or alternatively, a second pump 122 may be configured to pump the fluid mixture 112 from the first container 110 to the second container 118. Additionally or alternatively to pumping the fluid mixture 112 from the first container 110 to the second container 118, the second pump 122 may be used to pump the acid 116 into the second container 118. In some embodiments, the pump 108 and/or the pump 122 may facilitate the mixing of the fluid mixture 112 and the acid 116 by pumping the fluid mixture 112 into the second container 118 at a second flow rate. That is, for example, the second flow rate may cause a turbulence of the fluid mixture 112 and/or the acid 116 in the second container 118, which facilitates the mixing of the fluid mixture 112 and the acid 116. Examples of second flow rates that may be produced by the pump 108 pumping the fluid mixture 112 into the second container 118 include greater than about 0.5 gal/min, greater than about 0.75 gal/min, greater than about 1.0 gal/min, greater than about 1.25 gal/min, greater than about 1.5 gal/min, greater than about 1.75 gal/min, greater than about 2.0 gal/min and/or the like. However, these are only examples and not meant to be limiting.

Additionally or alternatively, to facilitate the combination of the fluid mixture 112 and the acid 116, a mixer 124 may be incorporated into, included in, and/or coupled to the second container 124. Before, during or after the fluid mixture 112 and the acid 116 are disposed in the second container 118, the mixer 124 may be started to facilitate the combination of the fluid mixture 112 and the acid 116 after the fluid mixture 112 and the acid 116 are combined in the second container 118. The mixer 124 may be any kind of mixing device that is capable of mixing liquids.

As stated above, the acid 116 may be used to lower the pH of the fluid mixture 112. In some embodiments, the acid 116 may be mixed with the fluid mixture 112 so that the combined solution, also referred to herein as the disinfectant solution 126, has a desired, neutral or relatively neutral pH. For example, the acid 116 may have a lower pKa than the fluid mixture 112 in order to lower the pH of the fluid mixture 112, so that the combined solution 126 has a pH of one or more of the following: a pH between about 5.0 and 7.0, a pH between about 6.0 and 7.0, and/or a pH of approximately 6.5 and/or the like. Examples of acids may be, but are not limited to, solid organic acids, such as glutaric acid, oxalic acid, malic, acid, citric acid, salicylic acid and/or the like and organic weak acids, such as citric acid monohydrate.

In some embodiments, to lower the pH of the fluid mixture 112, a specific quantity of acid 116 may be used. In one example, if citric acid is used as the solution to lower the pH of the fluid mixture 112 and if quantities of about 4 liters of water, about 23.3 grams (g) of TAED and about 16.6 g of sodium percarbonate were used to produce the fluid mixture 112, then about 16.6 g of citric acid may be added to the fluid mixture 112 to produce a combined solution 126 that has a pH between about 5.0 and 7.0. However, this example is only for illustrative purposes and is not meant to be limiting.

In some embodiments, the acid 116 may be included in a surfactant (e.g., Pluronic F68™ or Pluronic F68 LF, available from ThermoFisher Scientific) and combined with the fluid mixture 112, to facilitate the combination of the acid 116 and the fluid mixture 112. In one example, assuming quantities of about 4 liters of water, about 23.3 grams (g) of TAED and about 16.6 g of sodium percarbonate were used to produce the fluid mixture 112, then about 0.08 g of Pluronic F68 LF may be added to produce a combined solution 126, also referred to herein as a disinfectant solution 126.

In some embodiments, the acid 116 may be combined with the surfactant or other liquid that is at a lower temperature than the fluid mixture 112 so that the disinfectant solution 126 will have a lower temperature than the mixture 112. For example, the acid 116 may be combined with a surfactant or other liquid that is at a temperature so that the disinfectant solution 126 will have a temperature of approximately 20° C., 25° C., 30° C., 35° C., 40° C. and/or the like.

After the fluid mixture 112 and the acid 116 are combined to produce a disinfectant solution 126 with a desired pH, the disinfectant solution 126 may be used to disinfect a medical device 128. In embodiments, the second container 118 and the medical device 128 may be coupled to each other via one or more conduits (not shown). In embodiments, the disinfectant solution 126 may be transferred from the second container 118 to the medical device via the pump 108, the pump 122 and/or the pump 130. Examples of medical devices 128 include, but are not limited to: endoscopes and dental equipment.

In some embodiments, before the disinfectant solution 126 is used to disinfect a medical device 128, the disinfectant solution 126 may be filtered by a filter 132. In some embodiments, the filter 132 may be a filter capable of filtering out undissolved portions of the solid chemistries 102, 104 and/or other particulate matter in the disinfectant solution 126. In some embodiments, the disinfectant solution 126 may include portions of the solid chemistries 102, 104 because the filter 120 may not be included in the system 100 and/or the solid chemistries 102, 104 were not completely filtered by the filter 120. The filter 132 may be, for example, a 100 micron filter (i.e., the average pore size is 100 microns), a 20 micron filter (i.e., the average pore size is 20 microns), a 10 micron filter (i.e., the average pore size is 10 microns), a 5 micron filter (i.e., the average pore size is 5 microns), a 1 micron filter (i.e., the average pore size is 1 micron), a 0.5 micron filter (i.e., the average pore size is 0.5 microns), a 0.1 micron filter (i.e., the average pore size is 0.1 microns) and/or the like. While the filter 132 is illustrated as being disposed external to the second container 118, in some embodiments, the filter 132 may be coupled to an outlet of the second container 132, coupled to an inlet of the medical device 128, coupled to and/or incorporated into a conduit that connects the second container 118 to the medical device, incorporated into the second container 118, disposed between the second container 118 and the medical device 128 and/or the like.

As described above, due to the embodiments of FIG. 1, solid chemistries 102, 104 may be shipped to the facility that is disinfecting the medical device 128, so that the disinfectant solution 126 can be produced by the facility, instead of shipping liquid disinfectants to the facility that is disinfecting the medical device 128. As such, the disinfectant solution 126 may be used by the facility soon after the disinfectant solution 126 is produced (e.g., 5 minutes, 10 minutes, 30 minutes, 1 hour, 2 hours, 6 hours, 12 hours, 24 hours, 2 days, 3 days, 4 days and/or the like). Accordingly, the stability of the disinfectant solution 128 may not be a concern, compared to a disinfectant solution that is produced off site and shipped to the facility. Additionally or alternatively, another benefit compared to conventional disinfectant solutions that are produced off site may be that little or no acetic acid may be used in producing the disinfectant solution 128.

Figure 2:
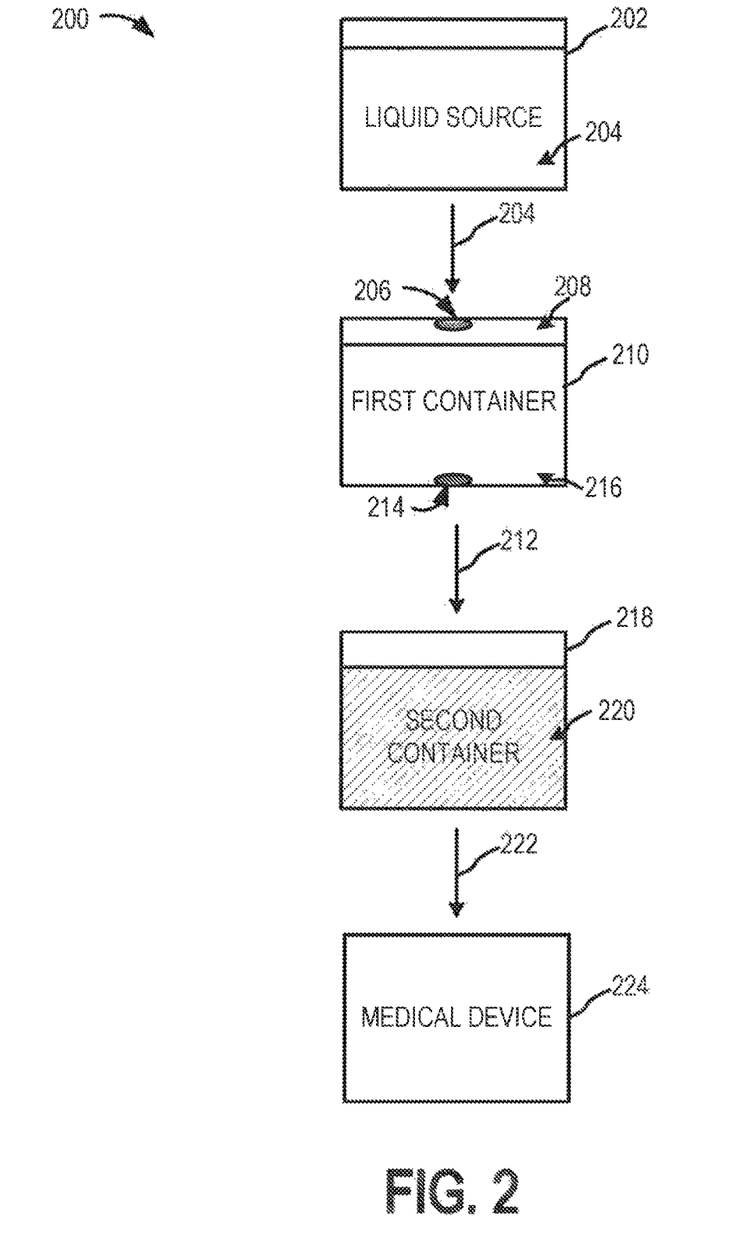
FIG. 2 is another schematic illustration of a disinfectant system, in accordance with some embodiments of the present disclosure.

FIG. 2 is another schematic illustration of a disinfectant system 200, in accordance with some embodiments of the present disclosure. The disinfectant system 200 includes a liquid source 202. In some embodiments, the liquid 204 may have some or all of the same characteristics of the liquid 106 discussed above in FIG. 1. For example, the liquid 204 may be water. In the illustrated embodiments, liquid 204 is released by the liquid source 202. After being released by the liquid source 202, the liquid 204 may fall, e.g., due to gravity, and/or may, be forced or injected into an orifice 206 located on the top portion 208 of a first container 210. In some embodiments, the liquid source 202 may be disposed on top of the first container 210 and/or a conduit (not shown) may couple the liquid source 202 to the orifice 206.

Figure 3:
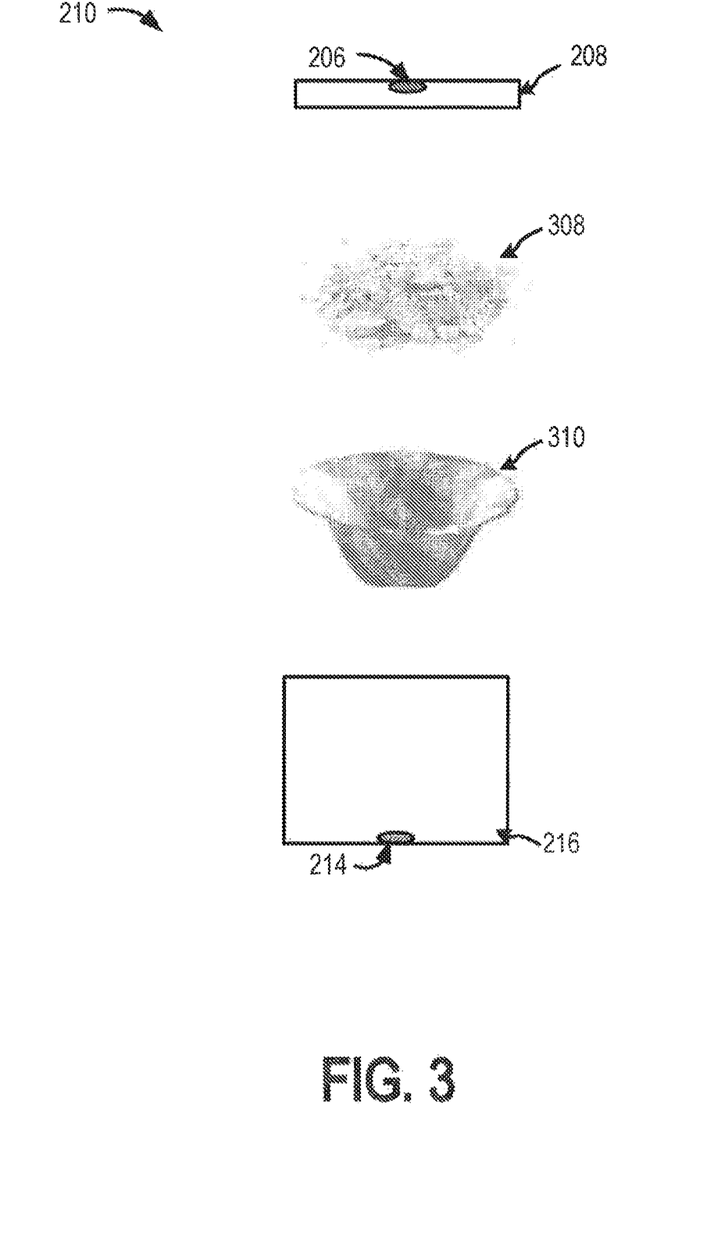
FIG. 3 is a schematic illustration of an expanded view of the first container depicted in FIG. 2, in accordance with embodiments of the present disclosure.

An illustrative exploded view of the first container 210 is depicted in FIG. 3. In some embodiments, the first container 210 includes one or more solid chemistries 308 (depicted in FIG. 3) and a filter 310 (depicted in FIG. 3). The solid chemistry 308 of the first container 210 may be disposed in the filter 310 of the first container 210. In some embodiments, the solid chemistry 308 and the liquid 204 may combine to produce a fluid mixture 212. In some embodiments, the solid chemistry 308 may have some or all of the same characteristics as the solid chemistries 102, 104 described above in relation to FIG. 1. For example, the solid chemistry 308 of the first container 210 may include sodium percarbonate and TAED. Additionally or alternatively to sodium percarbonate, the solid chemistry 308 may include sodium perborate. Additionally or alternatively, the filter 310 may have some or all of the same characteristics as the filter 120 depicted in FIG. 1. For example, the filter 310 may be a 100 micron filter, a 20 micron filter, a 10 micron filter, a 5 micron filter, a 1 micron filter, a 0.5 micron filter, a 0.1 micron filter and/or the like. Additionally or alternatively, the fluid mixture 212 may, have some or all of the same characteristics as the fluid mixture 112 depicted in FIG. 1. For example, the fluid mixture 212 may include peroxyacetic acid, as described below.

In an example where the liquid 204 is water and the solid chemistry 308 is sodium percarbonate and TAED, once the water 204 is deposited into the first container 210, the sodium percarbonate dissolves in the water to produce hydrogen peroxide, as described above in relation to FIG. 1. In some embodiments, the hydrogen peroxide may have concentrations between approximately 3000 ppm and 6000 ppm, specifically between 4000 ppm and 5000 ppm. After which, the hydrogen peroxide reacts with the TAED to produce peroxyacetic acid and DAED, as described above in relation to FIG. 1. In some embodiments, the force on the liquid 204 due to gravity and/or an external force applied to the liquid 204 (e.g., by a pump) may facilitate combining the liquid 204 and the solid chemistry 308.

In some embodiments, an amount of sodium percarbonate, TAED and water may be used to create a desired amount of peroxyacetic acid. For example, the amount of desired peroxyacetic acid produced by the disinfectant system 200 may be one or more of the following concentrations: between 500 parts per million (ppm) and about 22002200 ppm, between about 800 parts per million (ppm) and about 1600 ppm, between about 1000 ppm and about 1400 ppm, approximately 1200 ppm and/or the like. As another example, the amount of desired peroxyacetic acid produced may be greater than: about 500 ppm, about 800 ppm, about 1000 ppm, about 1200 ppm, about 1400 ppm, about 1600 ppm, and/or the like. As even another example, the amount of desired peroxyacetic acid produced may be between less than: about 1600 ppm, about 1400 ppm, about 1200 ppm, about 1000 ppm, 800 ppm, 500 ppm, and/or the like. However, these are only examples and not meant to be limiting. To produce peroxyacetic acid in quantities between 1200 ppm and 1500 ppm, about 0.5 liters of water may be used, about 2.91 grams (g) of TAED may be used and about 2.08 g of sodium percarbonate may be used. This example is given for illustration purposes only and is not meant to be limiting.

As stated above, the solid chemistry 308 may be disposed in a filter 310. In some embodiments, the filter 310 may allow the fluid mixture 212, (e.g., peroxyacetic acid) to pass through the filter 310, but retain the solid chemistry 308 before the liquid 204 is added to the solid chemistry 308. In some embodiments, the size of the filter 310 (e.g., a 100 micron filter, a 20 micron filter, a 10 micron filter, a 5 micron filter, a 1 micron filter, a 0.5 micron filter, a 0.1 micron filter and/or the like) may be selected so that the liquid 204 and/or the hydrogen peroxide is slowly transmitted through the filter 310. The slow transmission of the liquid 204 and/or the hydrogen peroxide may facilitate the combining of the liquid 204 and the solid chemistry 308 to produce the fluid mixture 212.

Once the solid chemistry 308 and the liquid 204 combine to produce the fluid mixture 212, the fluid mixture 212 is transmitted through a second orifice 214, on the bottom portion 216 of the first container 210, to a second container 218. In embodiments, the second orifice 214 may be sized to facilitate a slow exit of the fluid mixture 212 from the first container 210. The slow exit of the fluid mixture 212 from the first container 210 may facilitate the combining of the liquid 204 and the solid chemistry 308 to produce the fluid mixture 212, similar to selecting a filter 310 that facilitates a slow transmission of the fluid mixture 212 through the filter 310.

The second container 218 may include an acid 220 to facilitate lowering the pH of the fluid mixture 212, as described above in relation to FIG. 1, wherein the acid 220 is originally in powder form. That is, for example, the fluid mixture 212 and the acid 220 may combine to produce a combined solution 2:22, also referred to herein as a disinfectant solution 222. The acid 220 may have some or all of the same characteristics as the acid 116 depicted in FIG. 1. Examples of acids 220 may be, but are not limited to, solid organic acids, such as glutaric acid, oxalic acid, malic, acid, citric acid, salicylic acid and/or the like. In one example, assuming citric acid or citric acid monohydrate is used as the solution to lower the pH of the fluid mixture 212 and assuming quantities of about 0.5 liters of water, about 2.91 grams (g) of TAED and about 2.08 g of sodium percarbonate were used to produce the fluid mixture 212, then about 2.075 g of citric acid may be added to the fluid mixture 212 to produce a combined solution that has a pH between about 5.0 and 7.0. However, this example is only for illustrative purposes and is not meant to be limiting.

In some embodiments, the fluid mixture 212 may fall, due, e.g., to gravity, and/or may be forced out of the orifice 214. In some embodiments, the force on the fluid mixture 212 due to gravity and/or an external force applied to the fluid mixture 212 (e.g., by a pump) may facilitate combining the fluid mixture 212 and the acid 220. Additionally or alternatively, in some embodiments, a mixer (not shown) may be incorporated into, included in, and/or coupled to the second container 218. Before, during or after the fluid mixture 212 and the acid 220 are in the second container 220, the mixer may be started so that when the fluid mixture 212 and the acid 220 are in the second container, the combination of the fluid mixture 212 and the acid 220 may be facilitated by the mixer. The mixer may be any kind of mixing device that is capable of mixing liquids. Additionally or alternatively, in some embodiments, the acid 220 may be included in a surfactant (e.g., Pluronic F68™ or Pluronic F68 LF) to facilitate the combination of the fluid mixture 212 and the acid 220. Additionally or alternatively, the acid 220 may be combined with the surfactant or other liquid that is at a lower temperature than the fluid mixture 212 so that the disinfectant solution 222 will have a lower temperature than the fluid mixture 212. For example, the acid 220 may be combined with a surfactant or other liquid that is at a temperature so that the disinfectant solution 222 will have a temperature of approximately 20° C., 25° C., 30° C., 35° C., 40° C. and/or the like.

Additionally or alternatively, the combined solution 222 of the fluid mixture 212 and the acid 220 may have some or all of the same characteristics of the combined solution 126 depicted in FIG. 1. For example, after the fluid mixture 212 and the acid 220 are combined to produce the disinfectant solution 222 with a desired pH, the disinfectant solution 222 may be used to disinfect a medical device 224 (e.g., an endoscope and/or dental equipment).

As stated above, FIG. 3 is a schematic illustration of an expanded view of the first container 210 depicted in FIG. 2, in accordance with some embodiments of the present disclosure. The first container 210 includes a top portion 208 that includes the orifice 206. In some embodiments, the top portion 208 may be coupled to a bottom portion 216 of the first container 210 via a threading.

In the illustrated embodiment, a filter 310 is disposed in the bottom portion 216 of the first container 210. The filter 310 may have some or all of the same characteristics as the filter 120 depicted in FIG. 1. For example, the filter 310 may be a 100 micron filter, a 20 micron filter, a 10 micron filter, a 5 micron filter, a 1 micron filter, a 0.5 micron filter, a 0.1 micron filter and/or the like. In some embodiments, a stabilizing structure (not shown), for example, a wire structure, may be used to maintain the shape of the filter 310. The stabilizing structure may be used in addition to or in alternative to the bottom portion 216.

The first container 210 also includes a solid chemistry 308 disposed in the filter 310. Additionally or alternatively, the solid chemistry 308 may have some or all of the same characteristics as the solid chemistries 102, 104 depicted in FIG. 1. For example, the solid chemistry 308 may be and/or include sodium percarbonate and/or TAED and be of amounts to produce peroxyacetic acid in concentrations of one or more of the following: between 500 parts per million (ppm) and about 2200 ppm, between about 800 parts per million (ppm) and about 1600 ppm, between about 1000 ppm and about 1400 ppm, approximately 1200 ppm and/or the like.

As described above in relation to FIG. 2, a liquid (e.g., the liquid 106 depicted in FIG. 1, the liquid 204 depicted in FIG. 2) may be transmitted through the orifice 206 and combined with the solid chemistry 308 in the filter 310 of the first container 210. In some embodiments, sodium percarbonate (i.e., a component of the solid chemistry 310) may dissolve in water to produce hydrogen peroxide. The hydrogen peroxide may react with TAED (i.e., a component of the solid chemistry 308) to produce peroxyacetic acid and DAED. In some embodiments, the force on the liquid 204 due to gravity and/or an external force applied to the liquid may facilitate combining the liquid and the solid chemistry 308 to produce a mixture (e.g., the mixture 112 depicted in FIG. 1 and/or the fluid mixture 212 depicted in FIG. 2), which is then transmitted through the second orifice 214.

Figure 4:
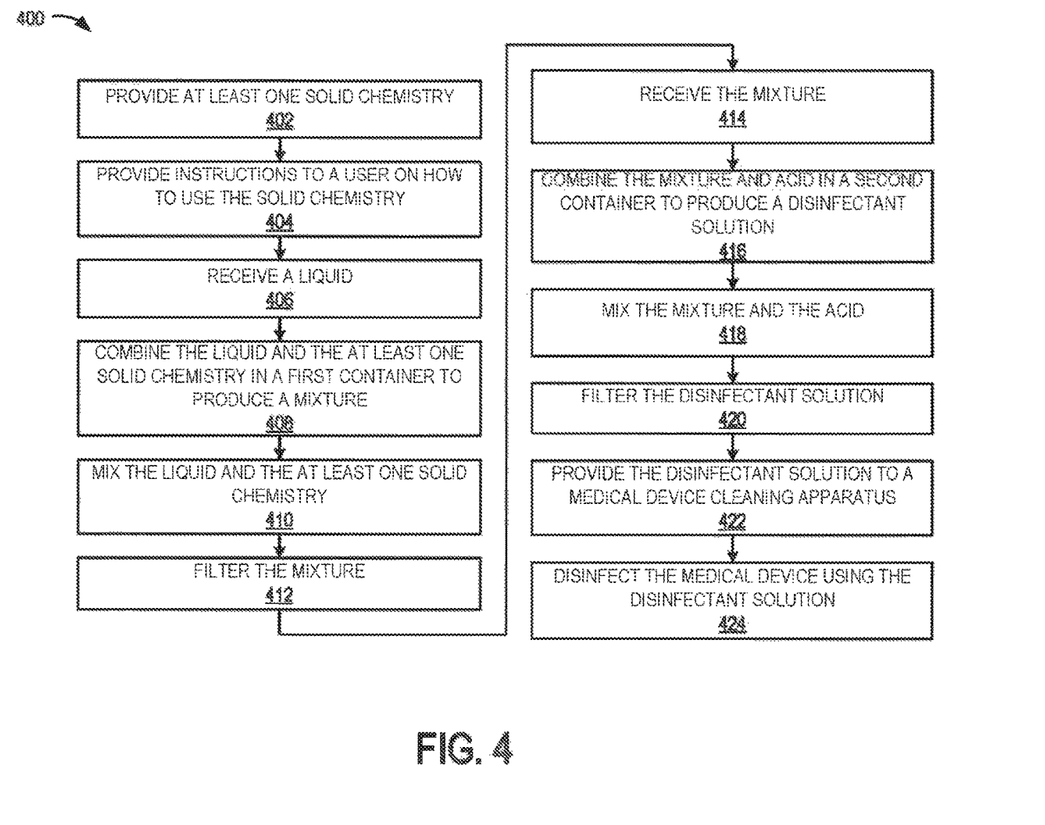
FIG. 4 is a flow diagram depicting one or more methods, in accordance with the embodiments of the disclosure.

FIG. 4 is a flow diagram depicting at least one method 400, in accordance with the some embodiments of the disclosure. The method 400 includes providing at least one solid chemistry (block 402). In some embodiments, the solid chemistry may have one or more of the same characteristics as the solid chemistries 102, 104 depicted in FIG. 1, and/or the solid chemistry 308 depicted in FIG. 3. For example, the solid chemistry may include sodium percarbonate and TAED. Additionally or alternatively to including sodium percarbonate, the solid chemistry may include sodium perborate. As another example, the solid chemistry may include amounts to produce peroxyacetic acid in concentrations of one or more of the following: between 500 parts per million (ppm) and about 2200 ppm, between about 800 parts per million (ppm) and about 1600 ppm, between about 1000 ppm and about 1400 ppm, approximately 1200 ppm and/or the like.

In some embodiments, the method 400 may include providing instructions to a user on how to use the solid chemistry to make a disinfectant solution (block 404). In some embodiments, the instructions may include one or more of the following steps of method 400. For example, by way of illustration and not of limitation, the instructions may include one or more of the following steps: 408, 410, 412, 414, 416, 418 and/or 420, each of which is discussed in more detail below.

In some embodiments, the method 400 may include receiving a liquid (block 406). In some embodiments, the liquid may be received by a first container (e.g., the first container 110 depicted in FIG. 1 and/or the first container 210 depicted in FIGS. 2 and 3) from a liquid source (e.g., the liquid source 202 depicted in FIG. 2) via a conduit and/or via an orifice (e.g., the orifice 206 depicted in FIGS. 2 and 3). In some embodiments a pump (e.g., the pump 108 depicted in FIG. 1) may pump the liquid from the liquid source to the first container. In some embodiments, the pump may pump the liquid from the liquid source to the first container at a flow rate of, for example, greater than about 0.5 gallons (gal)/minute (min), greater than about 0.75 gal/min, greater than about 1.0 gal/min, greater than about 1.25 gal/min, greater than about 1.5 gal/min, greater than about 1.75 gal/min, greater than about 2.0 gal/min and/or the like. Additionally or alternatively, gravity may facilitate the liquid being received by the first container, for example, as explained above in relation to FIG. 2.

In some embodiments, the liquid may have some or all of the same characteristics as the liquid 106 depicted in FIG. 1, and/or the liquid 204 depicted in FIG. 2. For example, the liquid 204 may be water, may be of a temperature greater than or equal to about 30° C., 35° C., 40° C., 50° C. 60° C., 70° C., 80° C., 90° C., 100° C. and/or the like, and may be of an amount to produce peroxyacetic acid in concentrations of one or more of the following: between 500 parts per million (ppm) and about 22002200 ppm, between about 800 parts per million (ppm) and about 1600 ppm, between about 1000 ppm and about 1400 ppm, approximately 1200 ppm and/or the like.

In some embodiments, the method 400 may include combining the liquid and the solid chemistry in a first container to produce a fluid mixture (block 408). In some embodiments, the fluid mixture produced from the combination of the liquid and the solid chemistry may have some or all of the same characteristics as the fluid mixture 112 depicted in FIG. 1 and/or the fluid mixture 212 depicted in FIG. 2. For example, the fluid mixture may be peroxyacetic acid and produced in concentrations of one or more of the following: between 500 parts per million (ppm) and about 2200 ppm, between about 800 parts per million (ppm) and about 1600 ppm, between about 1000 ppm and about 1400 ppm, approximately 1200 ppm and/or the like.

In some embodiments, the force on the liquid due to gravity and/or an external force applied to the liquid (e.g., by a pump) may facilitate combining the liquid and the solid chemistry due to the turbulence of the liquid. Additionally or alternatively, the method 400 may include mixing the liquid and the solid chemistry using a mixer (block 410). The mixer may be any kind of mixing device that is capable of mixing liquids. In some embodiments, the mixer may be incorporated into, included in, and/or coupled to the first container. After the liquid and solid chemistry are in the first container, the mixer may then mix the liquid and the solid chemistry to facilitate the combination of the liquid and the solid chemistry.

In some embodiments, the method 400 may include filtering the mixture (block 412). In some embodiments, a filter (e.g., the filter 120 depicted in FIG. 1 and/or the filter 308 depicted in FIG. 3) may be used to filter the mixture. For example, the filter may be a 100 micron filter, a 20 micron filter, a 10 micron filter, a 5 micron filter, a 1 micron filter, a 0.5 micron filter, a 0.1 micron filter and/or the like.

In some embodiments, the method 400 may include receiving the mixture (block 414). In some embodiments, the mixture may be received by a second container (e.g., the second container 118 depicted in FIG. 1 and/or the second container 218 depicted in FIG. 2) from the first container. In some embodiments, the mixture may be provided from the first container to the second container via a conduit and/or via an orifice (e.g., the orifice 214 depicted fix FIGS. 2 and 3). In some embodiments, a pump (e.g., the pump 108 and/or the pump 122 depicted in FIG. 1) may pump the mixture from the first container to the second container. In some embodiments, the pump may pump the mixture from the first container to the second container at a flow rate of, for example, greater than about 0.5 gallons (gal)/minute (min), greater than about 0.75 gal/min, greater than about 1.0 gal/min, greater than about 1.25 gal/min, greater than about 1.5 gal/min, greater than about 1.75 gal/min, greater than about 2.0 gal/min and/or the like. Additionally or alternatively, gravity may facilitate the mixture being received by the second container, for example, as explained above in relation to FIG. 2.

In some embodiments, the method 400 may include combining the mixture and an acid in the second container to produce a disinfectant solution (block 416). In some embodiments, the mixture may be combined with the acid to lower the pH of the mixture, as described above in relation to FIGS. 1-2. In some embodiments, the acid may have some or all of the same characteristics as the acid 116 depicted in FIG. 1 and/or the acid 220 depicted in FIG. 2. For example, a quantity of an acid may be used to lower the pH of the mixture, so that the combined solution has a pH of one or more of the following: a pH between about 5.0 and 7.0, a pH between about 6.0 and 7.0, a pH of approximately 6.5 and/or the like. Additionally or alternatively, in some embodiments, the acid may be included in a surfactant (e.g., Pluronic F63™ or Pluronic F68LF) to facilitate the combination of the fluid mixture and the acid. Additionally or alternatively, the acid may be combined with the surfactant or other liquid that is at a lower temperature than the fluid mixture so that the disinfectant solution will have a lower temperature than the fluid mixture. For example, the acid may be combined with a surfactant or other liquid that is at a temperature so that the disinfectant solution will have a temperature of approximately 20° C., 25° C., 30° C., 35° C., 40° C. and/or the like.

In some embodiments, the solid chemistries and the acid may be included in a single package and shipped to a facility that combines the solid chemistries with a liquid, as described above, and then combines the acid with the mixture resulting from the mixture of the solid chemistries and the liquid. In some embodiments, the solid chemistries and the acid are included in different compartments of the single package. As described above, this may eliminate the drawbacks of shipping a liquid disinfectant. For example, by shipping solid chemistries and an acid, shipping costs may be less than when shipping liquid disinfectants, the shelf life of the solid chemistries and the acid may be longer than liquid disinfectants, and the solid chemistries and the acid may be shipped via more methods than shipping liquid disinfectants (e.g., via air).

In some embodiments, the combined solution, also referred to herein as the disinfectant solution, produced from the combination of the mixture and the acid, may have some or all of the same characteristics as the disinfectant solution 126 depicted in FIG. 1 and/or the disinfectant solution 222 depicted in FIG. 2. For example, the mixture may be peroxyacetic acid and produced in concentrations of one or more of the following: between 500 parts per million (ppm) and about 2200 ppm, between about 800 parts per million (ppm) and about 1600 ppm, between about 1000 ppm and about 1400 ppm, approximately 1200 ppm and/or the like.

In some embodiments, the force due to gravity and/or an external force applied to the mixture (e.g., by a pump) may facilitate combining the mixture and the acid due to the turbulence of the mixture and the acid. Additionally or alternatively, the method 400 may include mixing the mixture and the acid (block 418). In some embodiments, the mixer may be incorporated into, included in, and/or coupled to the second container. Before, during or after the mixture and the acid are in the second container, the mixer may be started to facilitate the combination of the mixture and the acid to produce the disinfectant solution when the mixture and acid are in the second container. The mixer may be any kind of mixing device that is capable of mixing liquids. In some embodiments, the method 400 may include filtering the disinfectant solution (block 420). In some embodiments, a filter (e.g., the filter 132 depicted in FIG. 1) may be used to filter the mixture. For example, the filter may be a 100 micron filter, a 20 micron filter, a 10 micron filter, a 5 micron filter, a 1 micron filter, a 0.5 micron filter, a 0.1 micron filter and/or the like.

In some embodiments, the method 400 may include providing the disinfectant solution to a user and/or a medical device cleaning apparatus (e.g., an endoscope reprocessor) in order to disinfect a medical device (e.g., an endoscope) (block 422). In some embodiments, the method 400 may also include disinfecting the medical device using the disinfectant solution (block 424).

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. An apparatus configured to produce a disinfectant solution for use with disinfecting a medical device, the apparatus comprising:
   a first container configured to receive water, sodium percarbonate, and tetraacetylethylenediamine, wherein the water, the sodium percarbonate and the tetraacetylethylenediamine react within the first container to produce a mixture comprising peroxyacetic acid and having a pH between 9.0 and 14.0; and
   a second container in fluid communication with the first container, the second container configured to receive an acid and the mixture from the first container, wherein the mixture and the acid mix in the second container to produce a disinfectant solution having a pH between 5.0 and 7.0.

2. The apparatus of claim 1, wherein at least one of: the first container and the second container comprise a mixer configured to facilitate at least one of: dissolving of the sodium percarbonate in the water to produce hydrogen peroxide and mixing the hydrogen peroxide and the tetraacetylethylenediamine to produce the mixture comprising peroxyacetic acid.

3. The apparatus of claim 1, further comprising a pump coupled to at least one of: the first container and the second container, wherein the pump is configured to provide at least one of: the water to the first container at a first flow rate of at least 1 gallon per minute and the mixture to the second container at a second flow rate of at least 1 gallon per minute.

4. The apparatus of claim 3, wherein the first flow rate facilitates the dissolving of the sodium percarbonate in the water to produce hydrogen peroxide and the reaction of the hydrogen peroxide and the tetraacetylethylenediamine, and wherein the second flow rate facilitates the mixing of the mixture and the acid.

5. The apparatus of claim 1, further comprising a filter, wherein the filter is configured to at least partially remove undissolved solid from the mixture comprising peroxyacetic acid.

6. The apparatus of claim 5, wherein the first container functions as the filter.

7. The apparatus of claim 1, further comprising a filter configured to at least partially remove undissolved solid from the disinfectant solution.

8. The apparatus of claim 1, wherein the acid is citric acid and wherein the water has a temperature of at least 30° C.

9. The apparatus of claim 1, wherein amounts of the water, the sodium percarbonate and the tetraacetylethylenediamine are combined in the first container to produce at least one of: hydrogen peroxide in concentrations between 0 parts per million and 1000 parts per million and peroxyacetic acid in concentrations between 500 parts per million and 2200 parts per million.

10. An apparatus configured to produce a disinfectant solution for use with disinfecting a medical device, the apparatus comprising:
   a first container including sodium percarbonate and tetraacetylethylenediamine, the first container comprising a first aperture configured to receive water, wherein the water, the sodium percarbonate and the tetraacetylethylenediamine react within the first container to produce a mixture comprising peroxyacetic acid, wherein the first container is configured to filter undissolved portions of the sodium percarbonate and the tetraacetylethylenediamine and wherein the first container comprises a second aperture that the mixture exits through; and
   a second container configured to receive the mixture from the first container via the second aperture, the second container comprising an acid, wherein the mixture and the acid mix in the second container to produce a disinfectant solution having a pH between 5.0 and 7.0.

* * * * *